US005498413A

United States Patent [19]

Casal Alvarez et al.

[11] Patent Number: 5,498,413

[45] Date of Patent: Mar. 12, 1996

[54] RECOMBINANT SUBUNIT VACCINE AGAINST PORCINE PARVOVIRUS

[75] Inventors: Jose I. Casal Alvarez; Elena Cortes Valdes; Ana I. Ranz Casares; Carmen Vela Olmo; Kristian Dalsgaard, all of Madrid, Spain

[73] Assignee: Inmunologia Y Genetica, S.A., Madrid, Spain

[21] Appl. No.: 969,213

[22] PCT Filed: Mar. 26, 1992

[86] PCT No.: PCT/ES92/00032

§ 371 Date: Jan. 27, 1993

§ 102(e) Date: Jan. 27, 1993

[87] PCT Pub. No.: WO92/17589

PCT Pub. Date: Oct. 15, 1992

[30] Foreign Application Priority Data

Mar. 26, 1991 [ES] Spain .................................... 9100845

[51] Int. Cl.[6] .......................... A61K 39/23; C12N 15/35; C12N 15/63; C07K 14/015

[52] U.S. Cl. .................................... 424/233.1; 424/204.1; 424/818; 435/69.3; 435/320.1; 530/350; 530/826

[58] Field of Search ........................... 424/88, 89, 184.1, 424/185.1, 186.1, 204.1, 233.1; 435/69.3, 172.3, 320.1; 530/356, 395, 826

[56] References Cited

U.S. PATENT DOCUMENTS 4,971,793 11/1990 Wood et al. ......................... 424/233.1

FOREIGN PATENT DOCUMENTS 8802026 3/1988 WIPO .

OTHER PUBLICATIONS

Kajigaya, S. et al. Proc. Natl. Acad. Sci. USA 86:7601–7605 (1989).

Vasudevacharya, J. et al. Virology 173:368–377 (1989).

Molitor, T. W. et al. J. Virology 45(2):842–854 (1983).

Luckow, V. A. et al. Bio/Technology 6:47–55 (1988).

*Primary Examiner*—Hazel F. Sidberry
*Assistant Examiner*—Julie Krsek-Staples
*Attorney, Agent, or Firm*—Harrison & Egbert

[57] ABSTRACT

Method for the production of a subunit vaccine against porcine parvovirus (PPV). The method is comprised of a first step wherein a recombinant protein VP2 of PPV is obtained by using the replication of a recombinant baculovirus wherein the gene corresponding to VP2 has been previously inserted in cells of a permissive host. The protein VP2 obtained in this invention has the capacity of forming empty chimeric capsids with high immunogenicity and can be provided as a vaccine formulation for protecting pigs against PPV infection. The recombinant baculovirus AcMNPV.pPPVEx8 expresses the VP2 of PPV in conditions making possible the formation of pseudo-viral capsids.

6 Claims, 8 Drawing Sheets

PPVVP2 5' ——▶ 3'

Figure and Sequence I.D. No. 1A

| | | | | | | | | | | | | | | | | | | | |
|---|---|---|---|---|---|---|---|---|---|---|---|---|---|---|---|---|---|---|---|
| | | | | | | | | | 30 | | | | | | | | | | 60 |
| ATG | AGT | GAA | AAT | GTG | GAA | CAA | CAC | AAC | CCT | ATT | AAT | GCA | GCG | ACT | GAA | TTG | TCT | GCA | ACA |
| Met | Ser | Glu | Asn | Val | Glu | Gln | His | Asn | Pro | Ile | Asn | Ala | Ala | Thr | Glu | Leu | Ala | Ala | Thr |
| | | | | | | | | | 90 | | | | | | | | | | 120 |
| GGA | AAT | GAA | TCT | GGG | GGT | GGG | GGC | GGC | GGT | GGC | GGG | GGT | AGG | GGT | GCT | GGG | GGG | GTT | GGT |
| Gly | Asn | Glu | Ser | Gly | Gly | Gly | Gly | Gly | Gly | Gly | Gly | Gly | Arg | Gly | Ala | Gly | Gly | Val | Gly |
| | | | | | | | | | 150 | | | | | | | | | | 180 |
| GTG | TCT | ACA | GGT | AGT | TTC | AAT | AAT | CAA | ACA | GAA | TTT | CAA | TAC | TTG | GGG | GAG | GGC | TTG | GTT |
| Val | Ser | Thr | Gly | Ser | Phe | Asn | Asn | Gln | Thr | Glu | Phe | Gln | Tyr | Leu | Gly | Glu | Gly | Leu | Val |
| | | | | | | | | | 210 | | | | | | | | | | 240 |
| AGA | ATC | ACT | GCA | CAC | GCA | TCA | AGA | CTC | ATA | CAT | CTA | AAT | ATG | CCA | GAA | CAC | GAA | ACA | TAC |
| Arg | Ile | Thr | Ala | His | Ala | Ser | Arg | Leu | Ile | His | Leu | Asn | Met | Pro | Glu | His | Glu | Thr | Tyr |
| | | | | | | | | | 270 | | | | | | | | | | 300 |
| AAA | AGA | ATA | CAT | GTA | CTA | AAT | TCA | GAA | TCA | GGG | TCG | GCG | GGA | CAA | ATG | GTA | CAA | GAC | GAT |
| Lys | Arg | Ile | His | Val | Leu | Asn | Ser | Glu | Ser | Gly | Ser | Ala | Gly | Gln | Met | Val | Gln | Asp | Asp |
| | | | | | | | | | 330 | | | | | | | | | | 360 |
| GCA | CAC | ACA | CAA | ATG | GTA | ACA | CCT | TGG | TCA | CTA | ATA | GAT | GCT | AAC | GCA | TGC | GCA | GTG | TGG |
| Ala | His | Thr | Gln | Met | Val | Thr | Pro | Trp | Ser | Leu | Ile | Asp | Ala | Asn | Ala | Trp | Gly | Val | Trp |
| | | | | | | | | | 390 | | | | | | | | | | 420 |
| TTC | AAT | CCA | GCC | GAC | TGG | CAG | TTA | ATA | TCC | AAC | AAC | ATG | ACA | GAA | ATA | AAC | TTA | GTT | AGT |
| Phe | Asn | Pro | Ala | Asp | Trp | Gln | Leu | Ile | Ser | Asn | Asn | Met | Thr | Glu | Ile | Asn | Leu | Val | Ser |
| | | | | | | | | | 450 | | | | | | | | | | 480 |
| TTT | GAA | CAA | GCA | ATA | TTC | AAT | GTA | GTA | CTT | AAA | ACA | ATT | ACA | GAA | TCA | GCA | ACC | TCA | CCA |
| Phe | Glu | Gln | Ala | Ile | Phe | Asn | Val | Val | Leu | Lys | Thr | Ile | Thr | Glu | Ser | Ala | Thr | Ser | Pro |
| | | | | | | | | | 510 | | | | | | | | | | 540 |
| CCA | ACC | AAA | ATA | TAT | AAT | AAT | GAT | CTA | ACT | GCA | AGC | TTA | ATG | GTC | GCA | CTA | GAC | ACC | AAT |
| Pro | Thr | Lys | Ile | Tyr | Asn | Asn | Asp | Leu | Thr | Ala | Ser | Leu | Met | Val | Ala | Leu | Asp | Thr | Asn |

Figure and Sequence I.D. No. 1B

```
                                             570                                                        600
AAC ACA CTT CCA TAC ACA CCA GCA GCA CCT AGA AGT GAA ACA CTT GGT TTT TAT CCA TGG
Asn Thr Leu Pro Tyr Thr Pro Ala Ala Pro Arg Ser Glu Thr Leu Gly Phe Tyr Pro Trp

                                             630                                                        660
TTA CCT ACA AAA CCA ACT CAA TAC AGA TAT TAC CTA TCA TGC ATC AGA AAC CTA AAT CCA
Leu Pro Thr Lys Pro Thr Gln Tyr Arg Tyr Tyr Leu Ser Cys Ile Arg Asn Leu Asn Pro

                                             690                                                        720
CCA ACA TAC ACT GGA CAA TCA CAA CCA AAT AAC AGA CTC AAT ACA AAC AGG CTA CAC AGT
Pro Thr Tyr Thr Gly Gln Ser Gln Pro Asn Asn Arg Leu Asn Thr Asn Arg Leu His Ser

                                             750                                                        780
GAC ATT ATG TTC TAC ACA ATA GAA AAT GCA GTA CCA ATT CAT CTT CTA AGA ACA GGA GAT
Asp Ile Met Phe Tyr Thr Ile Glu Asn Ala Val Pro Ile His Leu Leu Arg Thr Gly Asp

                                             810                                                        840
GAA TTC TCC ACA GGA ATA TAT CAC TTT GAC ACA AAA CCA CTA AAA TTA ACT CAC TCA TGG
Glu Phe Ser Thr Gly Ile Tyr His Phe Asp Tyr Lys Pro Leu Lys Leu Thr His Ser Trp

                                             870                                                        900
CAA ACA AAC AGA TCT CTA GCA CTG CCT CCA AAA CTA CTA ACT GAA CCT ACC ACA GAA GGA
Gln Thr Asn Arg Ser Leu Gly Leu Pro Pro Lys Leu Leu Thr Glu Pro Thr Thr Glu Gly

                                             930                                                        960
GAC CAA CAC CCA GGA ACA CTA CCA GCA GCT AAC ACA AGA AAA GGT TAT CAC CAA ACA ATT
Asp Gln His Pro Gly Thr Leu Pro Ala Ala Asn Thr Arg Lys Gly Tyr His Gln Thr Ile

                                             990                                                        1020
AAT AAT AGC TAC ACA GAA GCA ACA GCA ATT AGG CCA GCT CAG GTA GGA TAT AAT ACA CCA
Asn Asn Ser Tyr Thr Glu Ala Thr Ala Ile Arg Pro Ala Gln Val Gly Tyr Asn Thr Pro
```

Figure and Sequence I.D. No. 1C 1050 1080
TAC ATG AAT TTT GAA TAC TCC AAT GGT GGA CCA TTT CTA ACT CCT ATA GTA CCA ACA GCA
Tyr Met Asn Phe Glu Tyr Ser Asn Gly Gly Pro Phe Leu Thr Pro Ile Val Pro Thr Ala 1110 1140
GAC ACA CAA TAT AAT GAT GAT GAA CCA AAT GGT GCT ATA AGA TTT ACA ATG GAT TAC CAA
Asp Thr Gln Tyr Asn Asp Asp Glu Pro Asn Gly Ala Ile Arg Phe Thr Met Asp Tyr Gln 1170 1200
CAT GGA CAC TTA ACC ACA TCT TCA CAA GAG CTA GAA AGA TAC ACA TTC AAT CCA CAA AGT
His Gly His Leu Thr Thr Ser Ser Gln Glu Leu Glu Arg Tyr Thr Phe Asn Pro Gln Ser 1230 1260
AAA TGT GGA AGA GCT CCA AAG CAA CAA TTT AAT CAA CAG GCA CCA CTA AAC CTA GAA AAT
Lys Cys Gly Arg Ala Pro Lys Gln Gln Phe Asn Gln Gln Ala Pro Leu Asn Leu Glu Asn 1290 1320
ACA AAT AAT GGA ACA CTT TTA CCT TCA GAT CCA ATA GGA GGG AAA TCT AAC ATG CAT TTC
Thr Asn Asn Gly Thr Leu Leu Pro Ser Asp Pro Ile Gly Gly Lys Ser Asn Met His Phe 1350 1380
ATG AAT ACA CTC AAT ACA TAT GGA CCA TTA ACA GCA CTA AAC AAT ACT GCA CCT GTA TTT
Met Asn Thr Leu Asn Thr Tyr Gly Pro Leu Thr Ala Leu Asn Asn Thr Ala Pro Val Phe 1410 1440
CCA AAT GGT CAA ATA TGG GAT AAA GAA CTT GAT ACA GAT CTA AAA CCT AGA CTA CAT GTT
Pro Asn Gly Gln Ile Trp Asp Lys Glu Leu Asp Thr Asp Leu Lys Pro Arg Leu His Val 1470 1500
ACA GCT CCA TTT GTT TGT AAA AAC AAT CCA CCA GGA CAA CTA TTT GTA AAA ATA GCA CCA
Thr Ala Pro Phe Val Cys Lys Asn Asn Pro Pro Gly Gln Leu Phe Val Lys Ile Ala Pro 1530 1560
AAC CTA ACA GAT GAT TTC AAT GCT GAC TCT CCT CAA CAA CCT AGA ATA ATA ACT TAT TCA
Asn Leu Thr Asp Asp Phe Asn Ala Asp Ser Pro Gln Gln Pro Arg Ile Ile Thr Tyr Ser

Figure and Sequence I.D. No. 1D

| | | | | | | | | | | | | | | | | | | | |
|---|---|---|---|---|---|---|---|---|---|---|---|---|---|---|---|---|---|---|---|
| | | | | | | | | | 1590 | | | | | | | | | | 1620 |
| AAC | TTT | TGG | TGG | AAA | GGA | ACA | CTA | ACA | TTC | ACA | GCA | AAA | ATG | AGA | TCC | AGT | AAT | ATG | TGG |
| Asn | Phe | Trp | Trp | Lys | Gly | Thr | Leu | Thr | Phe | Thr | Ala | Lys | Met | Arg | Ser | Ser | Asn | Met | Trp |
| | | | | | | | | | 1650 | | | | | | | | | | 1680 |
| AAC | CCT | ATT | CAA | CAA | CAC | ACA | ACA | ACA | GCA | GAA | AAC | ATT | GGT | AAA | TAT | ATT | CCT | ACA | AAT |
| Asn | Pro | Ile | Gln | Gln | His | Thr | Thr | Thr | Ala | Glu | Asn | Ile | Gly | Lys | Tyr | Ile | Pro | Thr | Asn |
| | | | | | | | | | 1710 | | | | | | | | | | 1740 |
| AAT | GGT | GGC | ATA | AAA | ATG | TTT | CCA | GAA | TAT | TCA | CAA | CTT | ATA | CCA | AGA | AAA | TTA | TAC | TAG |
| Ile | Gly | Gly | Ile | Lys | Met | Phe | Pro | Glu | Tyr | Ser | Gln | Leu | Ile | Pro | Arg | Lys | Leu | Tyr | End |

RECOMBINANT SUBUNIT VACCINE AGAINST PORCINE PARVOVIRUS

FIELD OF THE INVENTION

The present invention relates in general to viral proteins and to assays and vaccines using the same and, in particular, to a protein related to the major antigen (VP2) of the Porcine Parvovirus (PPV) capsid. Such protein was produced in an expression vector of baculoviruses multiplied in a cell culture of a permissive host.

BACKGROUND OF THE INVENTION

The Porcine Parvovirus (PPV) causes reproductive failure in swine, resulting in death and foetal mummification, still births and other reproductive failures in pregnant sows. (Joo & Johnson. 1976. Veterinary Bulletin 46, 653- 660; Mengeling. 1978. J. Am. Vet. Med. Assoc. 172, 1291- 1294). PPV is an autonomous parvovirus containing a single strand DNA molecule of approximately 5000 nucleotides (Mollitor et al. 1984. Virology 137, 241–254). The complete sequence of this genome has been recently described by our group (Ranz et al. 1989. J. Gen. Virol. 70, 2541–2553). Four virus-specific proteins have been described: three capsid proteins (VP1, VP2 and VP3 of Mr values 83000, 64000 and 60000 daltons, respectively) and one non structural protein NS1.

The PPV is related to the Kilham rat virus (KRV) group of autonomous parvoviruses formed by KRV, minute virus of mice (MVM), LuIII, H-1, Feline Panleukopenia virus (FPV), canine parvovirus (CPV) and the mink enteritis virus (MEV). These viruses share several common features with other autonomous parvoviruses:

1. There are two large open reading frames (ORFs).
2. The mRNAs from both ORFs are polyadenylated and 3'-coterminal.
3. The left ORF encodes non-capsid proteins which are necessary for viral DNA replication and the right ORF encodes the major capsid proteins as a nested set.

To date, there are several vaccines protecting from porcine parvovirus disease, which are based on conventional inactivation methods of the virus. However, every previous attempt of new vaccines production using recombinant proteins produced in procariotic microorganisms (v.g. *E. coli*) have failed. In this invention, a new process is described for obtaining a new kind of vaccines based on the immunogenic properties of the major protein VP2, expressed in a baculovirus system multiplied in a cell culture of a permissive host.

For the last years, our laboratory has been studying with great detail the molecular biology of PPV. The findings obtained thus are summarized in two pioneer publications:

A. Ranz, J. J. Manclus, E. Díaz Aroca, J. I. Casal. 1989. Porcine Parvovirus: DNA sequence and genome organization. J. Gen. virol. 70, 2541–25463.

J. I. Casal, E. Díaz, A. Ranz, J. J. Manclus. 1990. Construction of an infectious genomic clone of PPV. Effect of the 5' end on DNA replication. Virology 177, 764–767.

These publications are related with the knowledge of the viral DNA sequences encoding the proteins forming the vital capsid. These sequences allowed the identification of the gene that encodes the VP2 of PPV and its manipulation and insertion into the specific vectors to be expressed in the baculovirus system. This system allows a large-scale protein production based upon the replication of recombinant baculovirus derived from the *Autographa californica* nuclear polyhedrosis virus (AcMNPV) in insect cell cultures. The state of the art for these vectors is summed up in two scientific papers as follows:

Luckow, V. A. & Summers, M. D. 1988. Trends in the development of baculovirus expression vectors. Bio/Technology 6, 47–55.

Vialard et al. 1990. Synthesis of the membrane fusion and hemagglutinin proteins of Measles virus using a novel baculovirus vector containing the β-galactosidase gen. J. Virol. 64, 37–50.

The advantages of VP2 protein synthesis in a baculovirus vector are remarkable over the virus production in cell culture and subsequent purification, in the economic cost of the process and immunogenic antigen output. On the other hand, this invention avoids the sacrifice of animals to stablish primary cell cultures for virus replication, to keep viral reservoires and the usual hazard in virus handling, etc.

SUMMARY OF THE INVENTION

The present invencion puts forth a new process for producing a recombinant subunit vaccine to protect pigs from PPV. The new vaccine produced thus can contain:

1. The PPV VP2 protein produced in an expression vector of baculoviruses multiplied in a cell culture of a permissive host (this protein hereinafter optionally refered to as "VP2 hereof") or
2. Empty VP2 capsids formed by assembly of the VP2 hereof.

The VP2 protein hereof is singularly characterized in forming empty VP2 capsids, optionally incorporating other viral protein epitopes by genetic manipulation of the recombinant baculoviruses or chemical manipulation of the chimeric capsids.

The object of the invention is therefore a new process for obtaining a new improved subunit vaccine capable of protecting pigs from PPV infections. As aforesaid, the vaccine can either contain the VP2 protein hereof or empty VP2 capsids formed by the VP2 protein hereof, in as much as the empty VP2 capsids have an enhanced hemagglutinant activity and are highly immunogenic, excelling other recombinant proteins of these viruses produced hereto in any other vector. The new vaccines the invention provides and being one of its objects can contain either the said empty VP2 capsids with an immunologically acceptable diluent, with or without an adjuvant, or the VP2 protein hereof together with a diluent and an adjuvant.

Since the empty VP capsids can be chemically or genetically manipulated to introduce other unrelated viral protein or peptide epitopes therein, the use of the empty VP2 capsids both for PPV vaccinal purposes and modified to incorporate other epitopes, thereby to provide a polyvalent vaccine, are further additional objects of this invention.

The VP2 protein obtained with the invention and the VP2 capsids it can form can be useful in diagnosis to detect the presence of PPV specific antibodies or to induce polyclonal or monoclonal antibodies capable of PPV detection. The use of the VP2 protein hereof and of the VP2 capsids it can form for the above purposes is a further object of the present invention.

An additional object of this invention is a recombinant baculovirus and the process for obtaining the same, capable of producing a PPV VP2 recombinant protein identical to the viral protein; as shown in antigenic reactivity assays and other biological functionality assays. The recombinant baculovirus was called AcMNPV.pPPVEx8 and filed on 2.3.91 with the European Collection of Animal Cell Cultures, (ECACC), at Porton Down, Salisbury, Wiltshire SP4 OJG (Great Britain), accession number V91030213.

A further object of the invention is the new baculovirus transfer vector (pPPVEx8) containing the nucleic acid sequence coding for the VP2 hereof. With a process known as homologous recombination with AcMNPV wild-type genome this new vector leads to the said AcMNPV.pPPVEx8 recombinant baculovirus.

This invention also provides the nucleic acid sequence coding for the VP2 protein of the invention (FIG. 1 and SEQ ID. No. 1).

The empty VP2 capsids formed by autoassembly of the PPV recombinant VP2 proteins are yet another object of this invention.

BRIEF DESCRIPTION OF THE FIGURES

SEQ. ID. No. 1 and FIG. 1, shows the nucleotide sequence coding for the VP2 hereof and the amino acid sequence thereof. The nucleotide sequence is shown in the direction 5'→3' from left to right. The amino acids have been designated using the generally accepted three-letter code.

In FIG. 2, legend (a) refers to isolate agarose gel fragments, legend (b) refers to ligate, and legend (c) refers to phosphatase.

In FIG. 4, legend (a) refers to the logarithm of the titer, legend (b) refers to days post-immunization, and legend (c) refers to second immunization.

The antibody titre was measured by:

A) ELISA anti PPV virions (●—●).

B) PPV hemaglutination inhibition assays (HI) (■—■).

C) PPV Neutralization (▲—▲).

Figure 5:
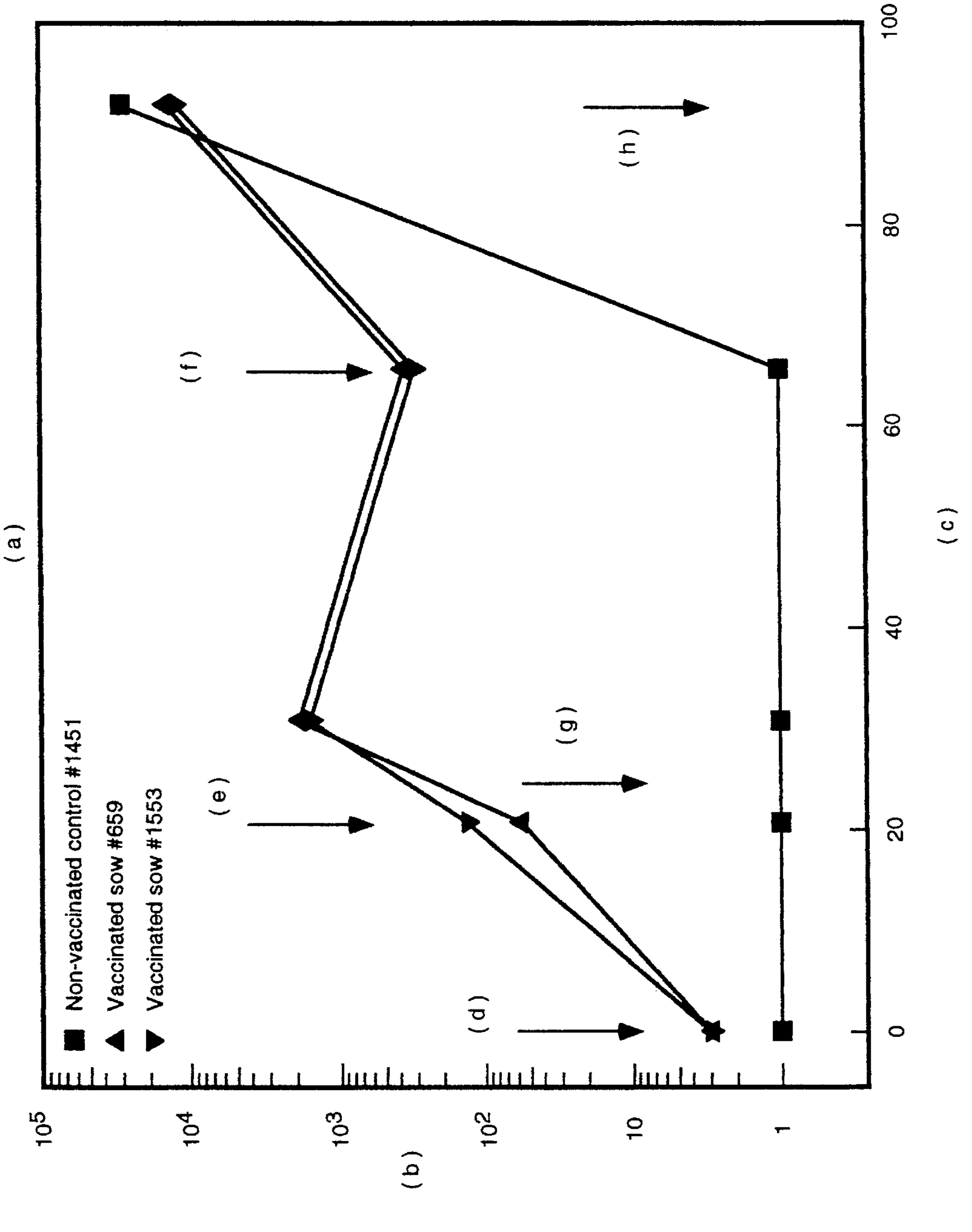

FIG. 5, shows the antibodies titre values against PPV obtained by ELISA in pregnant sows vaccinated with empty VP2 capsids (▲, ▼) and non-vaccinated (■), all of them were challenged with a PPV virulent strain. In FIG. 5, legend (a) refers to vaccination of pregnant sows with empty VP2 capsids formed by recombinant VP2 autoassembly, legend (b) refers to ELISA, antibody titres against PPV, legend (c) refers to days post-vaccination, legend (d) refers to the first vaccine, legend (e) refers to the second vaccine, legend (f) refers to challenge, legend (g) refers to artificial insemination, and legend (h) refers to necropsy.

DETAILED DESCRIPTION OF THE INVENTION

The invention provides a new process for obtaining a recombinant subunit vaccine serving to protect pigs against infections due to Porcine Parvovirus. The vaccine can contain the PPV VP2 recombinant protein produced in an expression vector of baculovirus multiplied in a cell culture of a lepidoptera or other permissive host, or empty VP2 capsids formed by aggregating the said recombinant VP2.

The invention also provides a recombinant baculovirus capable of expressing the PPV VP2 when inoculated in a permissive host, and the process for obtaining the said recombinant baculovirus.

The obtention of the recombinant baculovirus basically comprises the following steps:

a) Preparing the gene coding for the PPV VP2;

b) inserting the VP2 gene in a baculovirus transfer vector;

c) transfecting permissive host cells with the said baculovirus transfer vector holding the VP2 gene; and d) selecting the recombinant baculovirus expressing the PPV VP2 protein.

These steps will be described in detail hereinafter. The attached Sequence Listing is incorporated by reference hereto.

In a preferred embodiment the gene coding for the PPV VP2 protein is obtained from plasmid pPPV15, previously constructed in our laboratory, containing the sequences encoding for VP2, and inserted in the unique cloning site NheI of the AcMNPV-derived pJVP10Z plasmid, thereby to obtain a baculovirus transfer vector. In our invention the pPPVEx8 vector proved to have the PPV DNA adequately oriented to be expressed by the AcMNPV virus polyhedrin promoter.

The pPPVEx8 vector was used to co-transfect permissive host cells, with the AcMNPV virus wild-type DNA. Reference could, inter alia, be made to cells of lepidoptera or their larvae. In a preferred embodiment of this invention *Sodoptera frugiperda* (*S. frugiperda*) cells, generally from the Sf9 strain, were transfected using pPPVEx8, though it can naturally be assumed that similar results would be achieved transfecting other permissive cells for recombinant baculovirus replication.

After transfection, the recombinant baculoviruses were selected after removing and titrating the supernatant produced in a confluent monolayer of *S. frugiperda* cells. The blue plates with no trace of the viral polyhedrin under a light microscope were collected and back-titrated on *S. frugiperda* cells to obtain the recombinant baculoviruses. The AcMNPV.pPPVEx8 recombinant baculovirus is capable of expressing the PPV VP2 recombinant protein (VP2 hereof) and was filed with the ECACC, accession number V91030213.

A Dot Blot assay was used to verify that the VP2 gene had been adequately integrated into the said recombinant baculovirus genome.

The proteins expressed by the *S. frugiperda* cells infected with the recombinant baculovirus were analysed by electrophoresis in 8% to 15% SDS-polyacrylamide gradient gels and were stained with Coomassie blue to observe the presence of a protein with a virtual molecular weight of 64 KDa, equivalent to that of the viral VP2 in the recombinant virus plate. Immunodetection assays showed that the anti-PPV polyclonal antisera reacted with the VP2 expressed by the recombinant baculovirus. It can in light of these results be said that the VP2 hereof expressed by the recombinant baculovirus in *S. frugiperda* cells is antigenically undistinguishable from the viral VP2.

The VP2 protein obtained with the above-described process can be used for diagnosis purposes to detect the presence of specific PPV antibodies or to induce polyclonal or monoclonal antibodies capable of PPV detection. They can further be used to immunise animals to PPV. ELISA assays have shown that immunised animal sera recognised the viral antigens while hemagglutination inhibition assays (HI) showed that sera from animals immunised with the purified VP2 protein obtained with this invention offered HI titres of 1/320 when 4HA units of purified PPV were used as antigen. Thus, it can be said that the animals immunized with the VP2 obtained with our process are highly protected.

Based on the results obtained the VP2 protein expressed by the recombinant baculovirus vector hereof can be used to be formulated in vaccines in order to protect pigs from infections caused by PPV. These vaccines can be both passive and active. A passive vaccine could be obtained immunising animals with the recombinant and purified VP2 hereof and then isolating polyclonal antibodies from the said VP2 which could when purified be used in therapeutic or prophylactic applications. An active vaccine can be prepared resuspending the VP2 hereof in an immunologically acceptable diluent with an adjuvant.

It was submitted above that the VP2 protein obtained with the process of this invention is peculiar in that it can be aggregated, working pursuant to our conditions, and form empty VP2 capsids of regular and uniform structure and with a size of about 22 nm, as shown by electron microscopy. No-one had to date described the "in vitro" formation of empty VP2 capsids in Porcine Parvovirus using only the VP2 protein thereof. This much allows the recombinant VP2 proteins obtained to be easily purified. Furthermore, the empty VP capsids formed by VP2 assembly have an enhanced hemagglutination activity and are highly immunogenic, more so than other PPV recombinant proteins produced heretofore in other vectors. The empty VP capsids can hence be formulated to be used in vaccines capable of protecting animals from infections caused by PPV. Broadly speaking, an active vaccine can be prepared resuspending the empty VP capsids in an immunologically acceptable diluent, with or without an adjuvant. An important feature of these empty VP capsids, that could be obvious to someone skilled in the art, is that they can be chemically or genetically manipulated to introduce the protein epitopes of other viruses, infection of which is to be protected, thereby to work as a polyvalent vaccine.

Phosphate buffered saline (PBS) solutions or other saline-like solutions could be used as an immunologically acceptable diluent. The adjuvant used could be alumina gel suspensions or other adjuvants regularly used in formulating vaccines.

DETAILED DESCRIPTION OF A PREFERRED EMBODIMENT OF THE INVENTION (EXAMPLE)

1. Obtaining Recombinant Baculoviruses Expressing the PPV VP2 Gene 1.1. Preparing the VP2 Gene of PPV The complete PPV genome was cloned in our laboratory for the first time in the bacterial plasmid pUC18, obtaining the genomic clone pPPV10. The construction of this genomic clone has been described in "Construction of an infectious genomic clone of Porcine Parvovirus: Effect of the 5'-end on DNA replication", Casal et al. 1990. Virology 177, 764–767. As starting material we employed as original virus the PPV strain NADL-2, available at the American Type Culture Collection, Rockville, Md. (U.S.A.), accession number ATCC-VR742.

Figure 2:
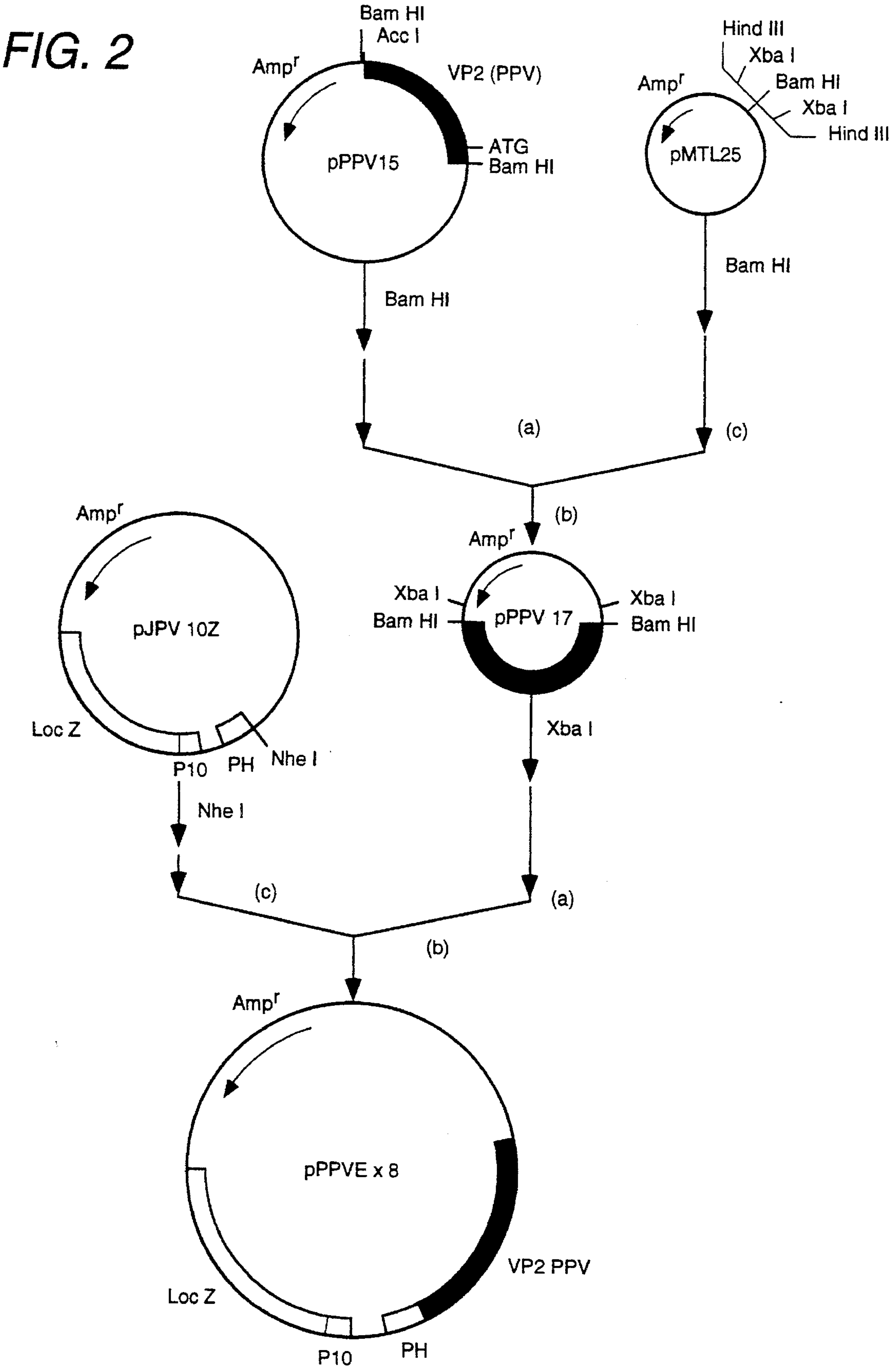
FIG. 2, shows the construction of the pPPVEx8 transfer vector, pointing out the appropriate manipulations for inserting the PPV VP2 gene in the pJVP10Z plasmid.

After manipulation, the pPPV10 genomic clone was used to obtain the pPPV15 plasmid (FIG. 2), which contains all the coding sequences (SEQ. ID. No. 1 and FIG. 1) for PPV VP2 in a DNA fragment of approximately 1.9 Kbp. The foreign DNA was inserted so as to allow its extraction in a single step, thanks to a BamHI restriction site. The inserted 1.9 Kbp DNA was isolated by electrophoresis in low melting agarose gels and inserted in a previously dephosphorilated and BamHI digested pMTL- 25 vector.

The plasmid so obtained was called pPPV17. It had the VP2 coding sequences from the PPV virus flanked by two XbaI restriction sites.

1.2. VP2 Gene Insertion in a Baculovirus Transfer Vector

The plasmidic vector with AcMNPV-derived NheI site, (pJVP10Z plasmid), (Vialard, J. Et al. J. Virol. 64, 37–50, 1990), was a gift of Dr. Cris Richardson (NRC. Quebec. Canada) and was used to clone the XbaI fragment obtained from the pPPV17 plasmid as described in FIG. 2. As the said figure shows, the XbaI pPPV17 fragment containing the PPV VP2 coding sequence (SEQ. ID. No. 1 and FIG. 1) was inserted into the pJVP10Z NheI site.

The plasmids thus obtained, containing the PPV VP2 gene, were purified according to the alkaline lysis method (Birmboim & Doly. Nucleic Acids Res. 7, 1513– 1523. 1979) and characterized by restriction endonuclease mapping.

The pPPVEx8 recombinant plasmid proved to have the PPV VP2 gene placed in the correct orientation to allow its expression by the AcMNPV virus polyhedrin promoter.

1.3. Recombinant Virus Transfection and Selection

*S. frugiperda* cells were transfected with infectious DNA mixtures of AcMNPV purified DNA and pPPVEx8 plasmidic DNA, according to the process described by Burand et al. Virology 101. 286–290. 1980. AcMNPV DNA (1 μg) purified according to Smith and Summers (Virology 123, 293–406. 1983), was mixed with two different quantities of plasmidic DNA (1 and 5 μg) and taken to 750 μl with a Hepes buffered saline solution (25 mM Hepes, pH 7.1, 140 mM NaCl and 125 mM $CaCl_2$). The DNA solution was inoculated on to monolayer cultures of $2\times10^6$ *S. frugiperda* cells and incubated for 4 h at room temperature. The supernatant was removed and 5 ml of medium containing 10% foetal calf serum were added.

After 4 days of incubation, supernatant was collected and plated on confluent monolayers of *S. frugiperda* cells. To improve the detection of recombinant plates, a X-gal blue indicator was added to the agarose. Blue plates showing no traces of occlusion bodies (viral polyhedrin) under a light microscope were collected and replated on *S. frugiperda* cells to obtain high-titre stocks of the recombinant viruses ($10^{7-8}$ pfu/ml).

The recombinant baculovirus was called AcMNPV.pPPVEx8 and filed at the European Collection of Animal Cell Cultures (ECACC), accession number V91030213.

Dot Blot Assay

A Dot Blot assay was made to determine whether the VP2 gene had been integrated in the recombinant baculovirus genome, as follows.

To obtain DNA from the recombinant baculovirus the *S. frugiperda* cells were infected with the said virus at a multiplicity of infection of 5 PFU/cell and incubated at 27° C. for 48 hours. The infected cells were collected, sonicated and centrifuged at 1000 rpm for 10 min to eliminate cell debris. The supernatant was used as starting material for the assays.

A volume of 100 μl was denatured with 10 μl of 1M NaOH, boiled for 5 min and placed immediately on ice. The mixture was neutralized with 10 μl of 1M $PO_4H_2Na$. A 20×SSC solution was added immediately to obtain a final 6×SSC concentration (SSC, solution saline citrate).

The solution was transferred to a nitrocellulose filter that had previously been moistened with 6×SSC. It was washed with more 6×SSC and dried at 37° C. for 30 min. The DNA was fixed to the nitrocellulose filter under an u.v. light for 2–3 min. The membranes were then hybridized with a specific probe of the VP2 DNA region labeled with Phosphorous-32 at 37° C. overnight. It was afterwards washed with decreasing SSC solutions and autoradiographed.

A strong sign of hybridization was observed only in those wells containing supernatants from the cultures infected with recombinant viruses, which indicated that the VP2 gene had been integrated in the viral genome.

3. Protein and Immunodetection Analysis

*S. frugiperda* cells were infected with the recombinant baculovirus at a multiplicity of 5 PFU/cell and incubated at 27° C. for 48 h. The cells were collected by centrifugation at 1000 rpm for 10 min, washed twice with phosphate buffered saline (PBS) solution pH 7.4 and resuspended at $1\times10^6$ cells/ml in lysis buffer (5% sodium dodecyl sulphate (SDS), 1% β-mercaptoethanol and 17.4% glycerol). The samples were charged in 8 to 15% SDS-polyacrylamide gradient gels for electrophoresis and stained with Coomassie blue or transferred to nitrocellulose membranes for immunodetection. The Coomassie blue showed the major presence of a protein with a molecular weight of 67 KDa, equivalent to that of the viral VP2, in the recombinant virus lane.

For immunodetection the proteins were transferred to nitrocellulose membranes in accordance with previously described methods (Burnette, Anal. Biochem. 112. 195–203, 1981. Towbin eta al., Proc. Natl. Acad. Sci. U.S.A. 76. 4350–4354. 1979). Protein transfer was made in a PhastSystem (Pharmacy) apparatus. In general 25 mA/gel were used for 10–15 min. The nitrocellulose strips were blocked with 3% powdered skim milk in 20 mM Tris HCl pH 7.5, 500 mM NaCl (TBS) for 30 min at room temperature. The strips were then incubated for an hour at room temperature with the first anti-PPV rabbit aniserum, washed with TBS-0.05% TWEEN-20™ for 30 min at room temperature and incubated for 1 h at room temperature with goat anti-rabbit serum labeled with biotin (1:500). The strips were washed again and allowed to react with streptavidin labeled with peroxidase (1:2000) for 30 min at room temperature. After a thorough wash, the filters were developed with a TBS solution containing 0.5 mg/ml of 4-chloro-1-naphthol (Sigma), 17% (v/v) of methanol and 0.015% of hydrogen peroxide in TBS until visible bands appeared. The reaction was stopped rinsing the strips with distilled water.

All the rabbit policlonal antisera that had been prepared against full PPV viral particles, reacted to the VP2 protein expressed by the recombinant baculovirus.

3.1. Recombinant Protein and Capsid Purification

*S. frugiperda* cells were infected with AcMNPV.pP-PVEx8 recombinant virus at a multiplicity of infection of 5–10 PFU/cell and incubated at 27° C. for 48–72 h. The cells were collected by centrifugation at 1000 rpm for 10 min, washed twice in a phosphate buffered saline solution pH 7.4 and resuspended at $2\times10^7$ cells/ml in a 25 mM bicarbonate buffer pH 9.5. The resuspended cells were broken down by sonication and centrifuged at 10.000 rpm for 10 min to eliminate cell debris. Supernatant containing the recombinant VP2 protein can be purified using its autoaggregating capacity to form empty VP2 capsids. They are to this end either purified by 20% ammonium sulphate precipitation or the empty VP2 capsids are centrifuged on CsCl gradients at 45.000 rpm for 14 h. Empty VP capsids offer a buoyant density (ρ) of 1.30 g/cm$^3$ when banded in CsCl gradient. Preparation purity was determined by electrophoresis in SDS-polyacrylamide gels as the method described above and VP2 protein purity turned out to be in excess of 99%.

4. Hemagglutination Activity

Hemagglutination activity of the VP2 protein was assayed in accordance with an already known method (Joo, H. S. et al. Aust. Vet. J. 52: 422–424. 1976). This functional activity is exclusively associated to the particulate character of the product, thereby clearly distinguishing the same from previous ones.

The results show that the preparation of VP2 capsids has an hemagglutination titre of $5.10^5$ units/ml.

5. Confirming the Presence of Empty VP2 Capsids by Electron Microscopy

Figure 3:
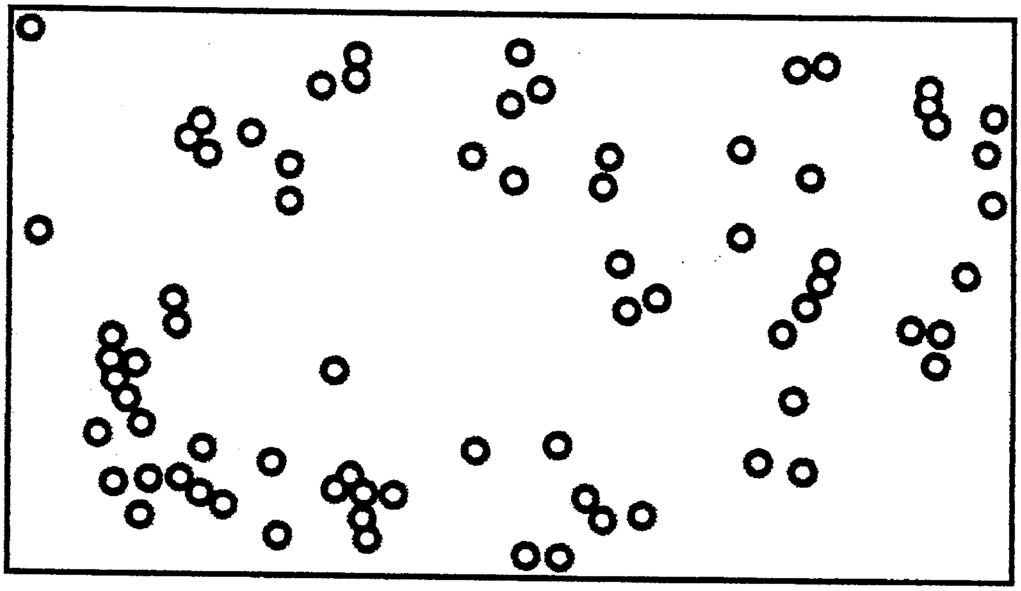
FIG. 3, shows the presence of empty VP 2 capsids formed by aggregation of the VP2 protein hereof, as observed under an electron microscope.

A purified VP2 preparation was stained by negative contrast with 2% uranyl acetate and observed under an electron microscope at a magnifying power of 40.000× 2.5, the presence of a large number of pseudo-viral particles of regular and uniform structure and with a size of roughly 22 nm was observed. (FIG. 3).

6. Immunizing Rabbits

Two New Zealand rabbits weighing 2 Kg were immunized three times intramuscularly with 100 μg of a purified VP2 preparation. The first time in a complete Freund adjuvant, the second and third times with an incomplete adjuvant. A week after the last immunization, the rabbits were bled and the sera obtained tested with an ELISA assay and an hemagglutination inhibition assay, as described hereinbelow.

6.1. Quantification of the Anti PPV Antibodies by ELISA and HI

The presence of PPV specific antibodies in the serum of immunized animals was determined by means of an indirect ELISA assay. The antigen used was both purified PPV virus and purified VP2 protein. Briefly, polystyrene plates were coated with 0.5 μg of virus or 0.25 μg/well of VP2 in 100 μl of carbonate buffer (0.05M, pH 9.6) at 4° C. overnight. The plates were washed with PBS (0.15M NaCl in 0.1M sodium phosphate pH 7.4) containing 0.05% Tween-20 and incubated with the anti-PPV rabbit antiserum for 2 h at 37° C., washed again and incubated with goat anti-rabbit IgG biotin-labeled. Then, streptavidin labeled with peroxidase was added to the antibody marked with biotin for 30 min at room temperature. The plates were washed again and the reaction developed with o-phenylenediamine as a substrate for the peroxidase, for 10 min in darkness, and read at 450 nm in a multichannel spectrophotometer.

For the rabbit sera, the ELISA titre achieved was 1/1600 against the VP2 protein and 1/3200 against the PPV complete virus.

The HI assay was made according to the standard methods previously described (Joo, H. S. et al Aust. Vet. J. 52: 422–424. 1976). The titre obtained was 1/320 when 4 HA units of purified PPV were used as antigen. Based on the good correlation observed between the HI and the protection titres of the animals against virus infection, we assume that the animals able to develop this titre have a high protection level.

7. Pig Immunization

Two pigs were immunized with purified preparations of empty VP2 capsids made of recombinant autoassembled VP2 proteins. One of the pigs was completely seronegative while the other one had a low level of antibodies, due to the fact that his mother had been previously vaccinated. Both pigs were kept in an isolation unit during the assay.

The vaccine was formulated by mixing the capsids (≈3μg) with a standard adjuvant system: 50% Alhydrogel (Superfos. Denmark)+500 μg QuilA (Superfos). All components were kept in standard concentrations except for the inactivated virus that was changed by PPV capsids. The pigs received two subcutaneous vaccinations: the first time the dose was 2 ml, and three weeks afterwards they were injected with a second dose of 1 ml. The serum was tested weekly, before vaccination and up to ten days after the last dose. The presence of anti-PPV antibodies in the pig serum was determined according to three different methods: (1) ELISA anti-PPV virion assay (2) Haemagglutination inhibition assay (Joo et al. 1976. Aust. Vet. J. 52: 422–424) and (3) PPV neutralization assay (Holm-Jensen M. 1991. Acta Vet. Scand. 22: 85–98).

Figure 4:
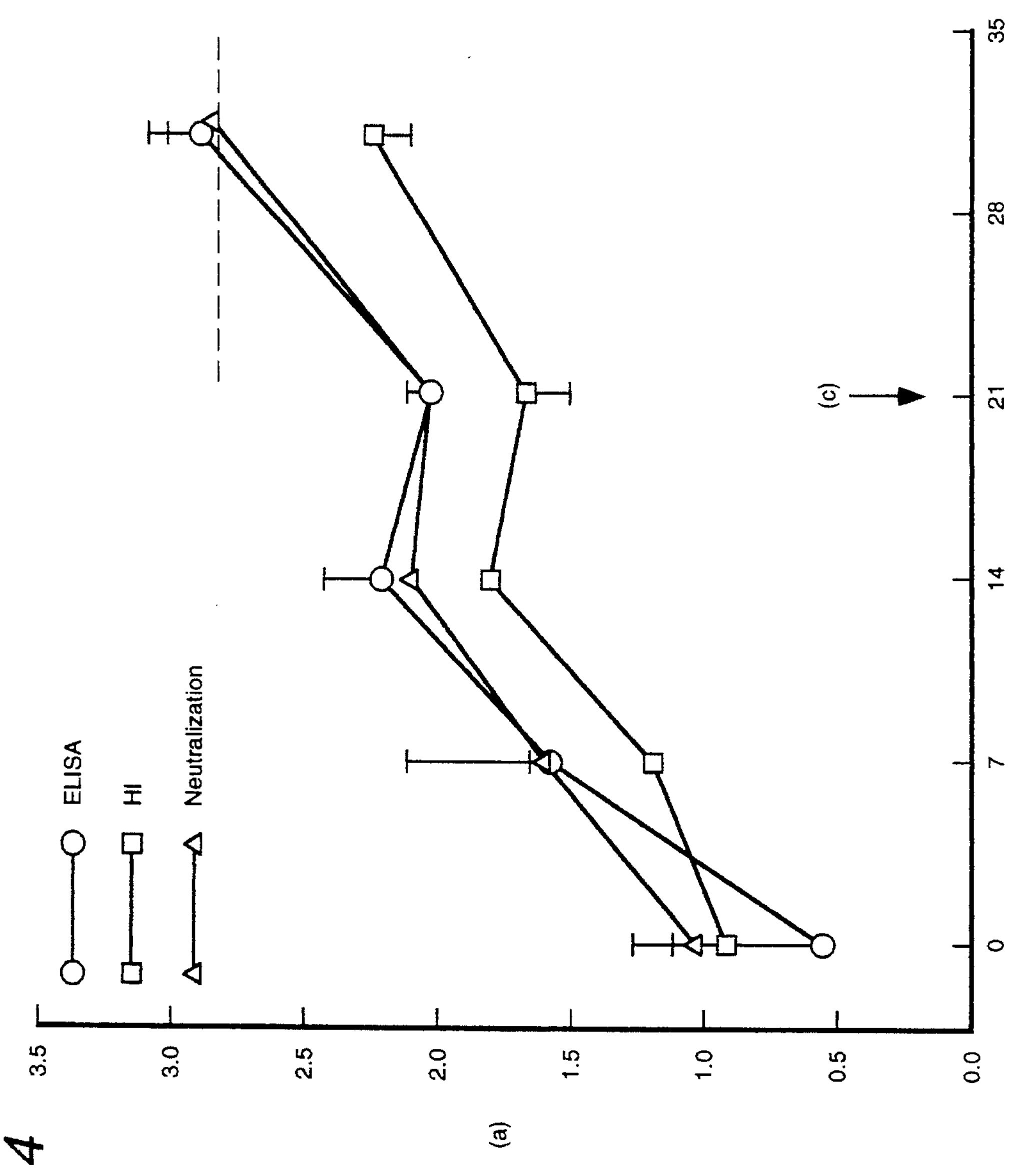
FIG. 4, shows the antibodies titre average values of sera from pigs immunized two times with 3 g of empty VP2 capsids adjuvanted with ALHYDROGEL™+ Quil-A.

The titres obtained with the capsids recombinant vaccine were similar (FIG. 4) to those normally obtained with the inactivated commercial vaccine. These results show that the PPV chimeric capsids are highly immunogenic and able to replace the inactivated virions. Even although one of the pigs kept residual maternal antibodies, the response to the vaccine was not inhibited, reaching levels similar to those obtained in the seronegative pig.

The response was achieved with a low dose of the recombinant capsids (≈3μg), which shows that the product shows high prospects of commercial application as vaccine.

8. "In Vivo" Protection Against a Virulent Virus

A challenge experiment was carried out to study the suitability of the recombinant VP2 capsids in the induction of protective immunity against PPV in pregnant sows.

Before artificial insemination, 2 seronegative sows were vaccinated with the same vaccine preparation described in the previous example. The antigen content, adyuvants and formulation of the vaccine were the same. Both sows were vaccinated twice with a 3 week interval. A seronegative pregnant sow was used as non-vaccinated control. At about 40 days of gestation the 3 pregnant sows were inoculated by intravenously route with $10^7$ $TCDI_{50}$ of a virulent PPV strain "839" (Sørensen and Askaa. 1981. Acta Vet. Scand. 22, 171–179). The three sows were sacrificed at 66 days of gestation.

Crown to rump length and gross pathological lesions (GPL) were recorded for each foetus. Blood samples of umbilical cord and sera from the foetuses were collected and checked for the presence of anti-PPV specific antibodies by an indirect immunofluorescence test (IFAT) (Sørensen et al. 1980, Acta Vet. Scand. 21, 312–317). Anti-PPV antibodies were also checked by a test of countercurrent immunoelectrophoresis. Beside this, these samples were checked also for IgM and IgG content using rocket electrophoresis (Dalsgaard et al. 1979. Acta Vet. Scand. 20, 312–320). In those cases where no blood from umbilical cord could be obtained, abdominal fluids or brain tissue extracts were used.

Foetal kidney, liver and lung tissues were collected and analyzed for the presence of PPV antigen by the ELISA test, routinely used in the State Veterinary Institute for Virus Research, Lindholm (SVIV) for PPV diagnosis. Also, blood samples of the sows were taken before vaccination, in the revaccination, 10 days after, in the time of the viral inoculation and in the sacrifice and checked for the presence of anti-PPV antibodies by the ELISA test previously mentioned.

The three sows remained healthy throughout the experiment. The antibody titers obtained during the experiment are shown in FIG. 5. The non-vaccinated sow remained seronegative until the viral challenge. After infection a dramatic increase in the anti-PPV antibody titers was observed in the necropsy. The two vaccinated sows show antibody titers that increase after vaccination and revaccination. These titers suffer a posterior slight increase due to the administration of virulent virus.

a) Foetuses of the Non-vaccinated Control

At necropsy, foetuses from the sow #1451 (non-vaccinated control) displayed typical lesions of intrauterine PPV infection (Bachmann et al. 1975, Infect Immunity, 12, 455–460; Joo et al. 1976; Arch. Virol. 51, 123–391; Nielsen et al. 1991. Vet. Microbiol. 28, 1–11). Four foetuses were alive. One of them did not show GPL, however, the other three displayed GPL of varying severity, typically discoloration, morbidity, with large volumes of ascitic fluids, edema, pulmonary stasis and erythema, thymic atrophy and enlargement of the liver. Other five foetuses were dead and had severe GPL including growth retardation. Universal extreme edema, hyperemia and pronounced tissue destruction. Three mummified foetuses had CR lengths of 11.5 to 12.5 cm indicating growth arrest at 57 days of gestation.

PPV antigen was detected in all the foetuses of the non-vaccinated sow, using the ELISA test previously described. In pleural fluids of three foetuses was detected antibody response (foetal) anti-PPV to the virus used for the challenge, as measured by IFAT and counter-current immunoelectroforesis. The presence in these samples of IgG and IgM was confirmed by "rocket" immunoelectrophoresis. The pig foetuses are able to induce an anti-PPV antibodies at 60 days of gestation (J. Nielsen et al. 1991, Vet. Microbiol. 28, 1–11).

b) Foetuses of the Vaccinated Sows

In the vaccinated sows, one of them had 10 foetuses and the other 8 foetuses. All of them were alive and normal in the necrospsy. All of them appeared healthy. No PPV antigen was detected in any of the foetuses. Neither anti-PPV antibodies were detected in blood or pleural fluid by any of the used techniques. The absence of IgG or IgM immunoglobulines was confirmed by rocket immunoelectrophoresis.

On the basis of these results above described it is possible to conclude that recombinant VP2 capsids of PPV expressed in the baculovirus/insect cells system are able to induce a protective immunity against an intravenous innoculation with virulent PPV virus in pregnant sows.

Based on these results, it is demonstrated that recombinant VP2 capsids may constitute the base for a new range of commercial vaccines useful on the control of PPV infection in pigs. In the same way, since the essential immunodominant epitopes of PPV are expressed on the empty VP2 capsids, these capsids can be useful as a reagent in the diagnosis of PPV infection in pigs, for instance, in kits for antibodies detection.

9. Vaccine Formulation Against the Infection Caused by PPV

It is possible to obtain a pasive vaccine immunizing animals with the recombinant VP2 capsids, purified as described in the present invention. Polyclonal antibodies, directed against this VP2, can be isolated from serum, milk or other animal bodily fluids. These antibodies can then be purified and used for therapeutics or prophylactic applications.

An active vaccine can be prepared resuspending the recombinant VP2 capsids described herein in an immunologically acceptable diluent such as PBS and an adjuvant such as ALHYDROGEL™ or QuilA. Initial and record injections or oral administration of the vaccinal solution can be used to confer immunity.

An active vaccine can also be prepared resuspending the empty VP2 capsids in an immunologically acceptable diluent with or without an adjuvant. Anyone skilled in the art will clearly see that these empty VP capsids formed only by VP2 can be chemically or genetically manipulated to introduce other viral protein epitopes and hence function as a polyvalent vaccine.

10. Conclusions

The AcMNPV.pPPVEx8 baculovirus is capable of producing a recombinant VP2 absolutely identical to the viral VP2 protein, as shown with the DNA sequence, molecular weight estimate and antigenic characterization. The VP2 obtained herein with our process is also remarkably capable of forming empty VP capsids, thereby providing the same with hemagglutination and immunogenic activity that are clearly greater than in other previously described recombinant proteins, as shown with the animal immunization tests herein described.

This enhanced immunogenic capacity can be used by those skilled in the art to present other viral protein epitopes, that can be introduced therein by either chemical or genetic manipulation of the recombinant baculoviruses.

The recombinant baculovirus has been filed with the European Collection of Animal Cell Cultures (ECACC) on Mar. 4, 1991.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1740 base pairs (580 amino acids)
( B ) TYPE: nucleic acid
( C ) STRANDEDNESS: single
( D ) TOPOLOGY: linear ( i i ) MOLECULE TYPE: genomic DNA ( i i i ) HYPOTHETICAL: Yes ( i v ) ANTI-SENSE: No ( v ) FRAGMENT TYPE: Complete VP2 sequence of PPV ( v i ) ORIGINAL SOURCE:
( A ) ORGANISM: Porcine Parvovirus
( B ) STRAIN: NADL/2

( v i i ) IMMEDIATE SOURCE:
( A ) LIBRARY: Genomic
( B ) CLONE: pPPV10

( x ) PUBLICATION INFORMATION:
( A ) AUTHORS:
Ranz, A.I.
Manclus, J.J.
D
az-Aroca, E.
Casal, J.I.
( B ) TITLE:
" PORCINE PARVOVIRUS: DNA SEQUENCE AND GENOME ORGANIZATION"
( C ) JOURNAL: The Journal of General Virology
( D ) VOLUME: 70
( F ) PAGES: 2541-2553
( G ) DATE: AUG, 1989
( K ) RELEVANT RESIDUES IN SEQ ID NO: From 1 to 1740

( x i ) SEQUENCE DESCRIPTION: SEQ ID. NO: 1:

```
ATG AGT GAA AAT GTG GAA CAA CAC AAC CCT ATT AAT GCA GCG ACT GAA     48
Met Ser Glu Asn Val Glu Gln His Asn Pro Ile Asn Ala Ala Thr Glu
  1             5                  10                  15

TTG TCT GCA ACA GGA AAT GAA TCT GGG GGT GGG GGC GGC GGT GGC GGG     96
Leu Ser Ala Thr Gly Asn Glu Ser Gly Gly Gly Gly Gly Gly Gly Gly
            20                  25                  30

GGT AGG GGT GCT GGG GGG GTT GGT GTG TCT ACA GGT AGT TTC AAT AAT    144
Gly Arg Gly Ala Gly Gly Val Gly Val Ser Thr Gly Ser Phe Asn Asn
         35                  40                  45

CAA ACA GAA TTT CAA TAC TTG GGG GAG GGC TTG GTT AGA ATC ACT GCA    192
Gln Thr Glu Phe Gln Tyr Leu Gly Glu Gly Leu Val Arg Ile Thr Ala
     50                  55                  60
```

-continued

| | | | | | | | | | | | | | | | | |
|---|---|---|---|---|---|---|---|---|---|---|---|---|---|---|---|---|
| CAC | GCA | TCA | AGA | CTC | ATA | CAT | CTA | AAT | ATG | CCA | GAA | CAC | GAA | ACA | TAC | 240 |
| His | Ala | Ser | Arg | Leu | Ile | His | Leu | Asn | Met | Pro | Glu | His | Glu | Thr | Tyr | |
| 65 | | | | | 70 | | | | | 75 | | | | | 80 | |
| AAA | AGA | ATA | CAT | GTA | CTA | AAT | TCA | GAA | TCA | GGG | TCG | GCG | GGA | CAA | ATG | 288 |
| Lys | Arg | Ile | His | Val | Leu | Asn | Ser | Glu | Ser | Gly | Ser | Ala | Gly | Gln | Met | |
| | | | | 85 | | | | | 90 | | | | | 95 | | |
| GTA | CAA | GAC | GAT | GCA | CAC | ACA | CAA | ATG | GTA | ACA | CCT | TGG | TCA | CTA | ATA | 336 |
| Val | Gln | Asp | Asp | Ala | His | Thr | Gln | Met | Val | Thr | Pro | Trp | Ser | Leu | Ile | |
| | | | 100 | | | | | 105 | | | | | 110 | | | |
| GAT | GCT | AAC | GCA | TGG | GGA | GTG | TGG | TTC | AAT | CCA | GCG | GAC | TGG | CAG | TTA | 384 |
| Asp | Ala | Asn | Ala | Trp | Gly | Val | Trp | Phe | Asn | Pro | Ala | Asp | Trp | Gln | Leu | |
| | | 115 | | | | | 120 | | | | | 125 | | | | |
| ATA | TCC | AAC | AAC | ATG | ACA | GAA | ATA | AAC | TTA | GTT | AGT | TTT | GAA | CAA | GCA | 432 |
| Ile | Ser | Asn | Asn | Met | Thr | Glu | Ile | Asn | Leu | Val | Ser | Phe | Glu | Gln | Ala | |
| | 130 | | | | | 135 | | | | | 140 | | | | | |
| ATA | TTC | AAT | GTA | GTA | CTT | AAA | ACA | ATT | ACA | GAA | TCA | GCA | ACC | TCA | CCA | 480 |
| Ile | Phe | Asn | Val | Val | Leu | Lys | Thr | Ile | Thr | Glu | Ser | Ala | Thr | Ser | Pro | |
| 145 | | | | | 150 | | | | | 155 | | | | | 160 | |
| CCA | ACC | AAA | ATA | TAT | AAT | AAT | GAT | CTA | ACT | GCA | AGC | TTA | ATG | GTC | GCA | 528 |
| Pro | Thr | Lys | Ile | Tyr | Asn | Asn | Asp | Leu | Thr | Ala | Ser | Leu | Met | Val | Ala | |
| | | | | 165 | | | | | 170 | | | | | 175 | | |
| CTA | GAC | ACC | AAT | AAC | ACA | CTT | CCA | TAC | ACA | CCA | GCA | GCA | CCT | AGA | AGT | 576 |
| Leu | Asp | Thr | Asn | Asn | Thr | Leu | Pro | Tyr | Thr | Pro | Ala | Ala | Pro | Arg | Ser | |
| | | | 180 | | | | | 185 | | | | | 190 | | | |
| GAA | ACA | CTT | GGT | TTT | TAT | CCA | TGG | TTA | CCT | ACA | AAA | CCA | ACT | CAA | TAC | 624 |
| Glu | Thr | Leu | Gly | Phe | Tyr | Pro | Trp | Leu | Pro | Thr | Lys | Pro | Thr | Gln | Tyr | |
| | | 195 | | | | | 200 | | | | | 205 | | | | |
| AGA | TAT | TAC | CTA | TCA | TGC | ATC | AGA | AAC | CTA | AAT | CCA | CCA | ACA | TAC | ACT | 672 |
| Arg | Tyr | Tyr | Leu | Ser | Cys | Ile | Arg | Asn | Leu | Asn | Pro | Pro | Thr | Tyr | Thr | |
| | 210 | | | | | 215 | | | | | 220 | | | | | |
| GGA | CAA | TCA | CAA | CCA | AAT | AAC | AGA | CTC | AAT | ACA | AAC | AGG | CTA | CAC | AGT | 720 |
| Gly | Gln | Ser | Gln | Pro | Asn | Asn | Arg | Leu | Asn | Thr | Asn | Arg | Leu | His | Ser | |
| 225 | | | | | 230 | | | | | 235 | | | | | 240 | |
| GAC | ATT | ATG | TTC | TAC | ACA | ATA | GAA | AAT | GCA | GTA | CCA | ATT | CAT | CTT | CTA | 768 |
| Asp | Ile | Met | Phe | Tyr | Thr | Ile | Glu | Asn | Ala | Val | Pro | Ile | His | Leu | Leu | |
| | | | | 245 | | | | | 250 | | | | | 255 | | |
| AGA | ACA | GGA | GAT | GAA | TTC | TCC | ACA | GGA | ATA | TAT | CAC | TTT | GAC | ACA | AAA | 816 |
| Arg | Thr | Gly | Asp | Glu | Phe | Ser | Thr | Gly | Ile | Tyr | His | Phe | Asp | Thr | Lys | |
| | | | 260 | | | | | 265 | | | | | 270 | | | |
| CCA | CTA | AAA | TTA | ACT | CAC | TCA | TGG | CAA | ACA | AAC | AGA | TCT | CTA | GGA | CTG | 864 |
| Pro | Leu | Lys | Leu | Thr | His | Ser | Trp | Gln | Thr | Asn | Arg | Ser | Leu | Gly | Leu | |
| | | 275 | | | | | 280 | | | | | 285 | | | | |
| CCT | CCA | AAA | CTA | CTA | ACT | GAA | CCT | ACC | ACA | GAA | GGA | GAC | CAA | CAC | CCA | 912 |
| Pro | Pro | Lys | Leu | Leu | Thr | Glu | Pro | Thr | Thr | Glu | Gly | Asp | Gln | His | Pro | |
| | 290 | | | | | 295 | | | | | 300 | | | | | |
| GGA | ACA | CTA | CCA | GCA | GCT | AAC | ACA | AGA | AAA | GGT | TAT | CAC | CAA | ACA | ATT | 960 |
| Gly | Thr | Leu | Pro | Ala | Ala | Asn | Thr | Arg | Lys | Gly | Tyr | His | Gln | Thr | Ile | |
| 305 | | | | | 310 | | | | | 315 | | | | | 320 | |
| AAT | AAT | AGC | TAC | ACA | GAA | GCA | ACA | GCA | ATT | AGG | CCA | GCT | CAG | GTA | GGA | 1008 |
| Asn | Asn | Ser | Tyr | Thr | Glu | Ala | Thr | Ala | Ile | Arg | Pro | Ala | Gln | Val | Gly | |
| | | | | 325 | | | | | 330 | | | | | 335 | | |
| TAT | AAT | ACA | CCA | TAC | ATG | AAT | TTT | GAA | TAC | TCC | AAT | GGT | GGA | CCA | TTT | 1056 |
| Tyr | Asn | Thr | Pro | Tyr | Met | Asn | Phe | Glu | Tyr | Ser | Asn | Gly | Gly | Pro | Phe | |
| | | | 340 | | | | | 345 | | | | | 350 | | | |
| CTA | ACT | CCT | ATA | GTA | CCA | ACA | GCA | GAC | ACA | CAA | TAT | AAT | GAT | GAT | GAA | 1104 |
| Leu | Thr | Pro | Ile | Val | Pro | Thr | Ala | Asp | Thr | Gln | Tyr | Asn | Asp | Asp | Glu | |
| | | 355 | | | | | 360 | | | | | 365 | | | | |
| CCA | AAT | GGT | GCT | ATA | AGA | TTT | ACA | ATG | GAT | TAC | CAA | CAT | GGA | CAC | TTA | 1152 |
| Pro | Asn | Gly | Ala | Ile | Arg | Phe | Thr | Met | Asp | Tyr | Gln | His | Gly | His | Leu | |
| | 370 | | | | | 375 | | | | | 380 | | | | | |

-continued

| | | | | | | | | | | | | | | | | |
|---|---|---|---|---|---|---|---|---|---|---|---|---|---|---|---|---|
| ACC | ACA | TCT | TCA | CAA | GAG | CTA | GAA | AGA | TAC | ACA | TTC | AAT | CCA | CAA | AGT | 1200 |
| Thr | Thr | Ser | Ser | Gln | Glu | Leu | Glu | Arg | Tyr | Thr | Phe | Asn | Pro | Gln | Ser | |
| 385 | | | | | 390 | | | | | 395 | | | | | 400 | |
| AAA | TGT | GGA | AGA | GCT | CCA | AAG | CAA | CAA | TTT | AAT | CAA | CAG | GCA | CCA | CTA | 1248 |
| Lys | Cys | Gly | Arg | Ala | Pro | Lys | Gln | Gln | Phe | Asn | Gln | Gln | Ala | Pro | Leu | |
| | | | | 405 | | | | | 410 | | | | | 415 | | |
| AAC | CTA | GAA | AAT | ACA | AAT | AAT | GGA | ACA | CTT | TTA | CCT | TCA | GAT | CCA | ATA | 1296 |
| Asn | Leu | Glu | Asn | Thr | Asn | Asn | Gly | Thr | Leu | Leu | Pro | Ser | Asp | Pro | Ile | |
| | | | 420 | | | | | 425 | | | | | 430 | | | |
| GGA | GGG | AAA | TCT | AAC | ATG | CAT | TTC | ATG | AAT | ACA | CTC | AAT | ACA | TAT | GGA | 1344 |
| Gly | Gly | Lys | Ser | Asn | Met | His | Phe | Met | Asn | Thr | Leu | Asn | Thr | Tyr | Gly | |
| | | 435 | | | | | 440 | | | | | 445 | | | | |
| CCA | TTA | ACA | GCA | CTA | AAC | AAT | ACT | GCA | CCT | GTA | TTT | CCA | AAT | GGT | CAA | 1392 |
| Pro | Leu | Thr | Ala | Leu | Asn | Asn | Thr | Ala | Pro | Val | Phe | Pro | Asn | Gly | Gln | |
| | 450 | | | | | 455 | | | | | 460 | | | | | |
| ATA | TGG | GAT | AAA | GAA | CTT | GAT | ACA | GAT | CTA | AAA | CCT | AGA | CTA | CAT | GTT | 1440 |
| Ile | Trp | Asp | Lys | Glu | Leu | Asp | Thr | Asp | Leu | Lys | Pro | Arg | Leu | His | Val | |
| 465 | | | | | 470 | | | | | 475 | | | | | 480 | |
| ACA | GCT | CCA | TTT | GTT | TGT | AAA | AAC | AAT | CCA | CCA | GGA | CAA | CTA | TTT | GTA | 1488 |
| Thr | Ala | Pro | Phe | Val | Cys | Lys | Asn | Asn | Pro | Pro | Gly | Gln | Leu | Phe | Val | |
| | | | | 485 | | | | | 490 | | | | | 495 | | |
| AAA | ATA | GCA | CCA | AAC | CTA | ACA | GAT | GAT | TTC | AAT | GCT | GAC | TCT | CCT | CAA | 1536 |
| Lys | Ile | Ala | Pro | Asn | Leu | Thr | Asp | Asp | Phe | Asn | Ala | Asp | Ser | Pro | Gln | |
| | | | 500 | | | | | 505 | | | | | 510 | | | |
| CAA | CCT | AGA | ATA | ATA | ACT | TAT | TCA | AAC | TTT | TGG | TGG | AAA | GGA | ACA | CTA | 1584 |
| Gln | Pro | Arg | Ile | Ile | Thr | Tyr | Ser | Asn | Phe | Trp | Trp | Lys | Gly | Thr | Leu | |
| | | 515 | | | | | 520 | | | | | 525 | | | | |
| ACA | TTC | ACA | GCA | AAA | ATG | AGA | TCC | AGT | AAT | ATG | TGG | AAC | CCT | ATT | CAA | 1632 |
| Thr | Phe | Thr | Ala | Lys | Met | Arg | Ser | Ser | Asn | Met | Trp | Asn | Pro | Ile | Gln | |
| | 530 | | | | | 535 | | | | | 540 | | | | | |
| CAA | CAC | ACA | ACA | ACA | GCA | GAA | AAC | ATT | GGT | AAA | TAT | ATT | CCT | ACA | AAT | 1680 |
| Gln | His | Thr | Thr | Thr | Ala | Glu | Asn | Ile | Gly | Lys | Tyr | Ile | Pro | Thr | Asn | |
| 545 | | | | | 550 | | | | | 555 | | | | | 560 | |
| ATT | GGT | GGC | ATA | AAA | ATG | TTT | CCA | GAA | TAT | TCA | CAA | CTT | ATA | CCA | AGA | 1728 |
| Ile | Gly | Gly | Ile | Lys | Met | Phe | Pro | Glu | Tyr | Ser | Gln | Leu | Ile | Pro | Arg | |
| | | | | 565 | | | | | 570 | | | | | 575 | | |
| AAA | TTA | TAC | TAG | | | | | | | | | | | | | 1740 |
| Lys | Leu | Tyr | End | | | | | | | | | | | | | |
| | | | 580 | | | | | | | | | | | | | |

We claim:

1. A recombinant subunit vaccine to protect pigs against PPV infection consisting essentially of:

an immunizing quantity of empty VP2 capsids formed by autoassembly of only PPV recombinant VP2 protein; and a diluent and an adjuvant, being immunologically acceptable.

2. The vaccine as in claim 1, said PPV recombinant VP2 protein is expressed by a recombinant baculovirus in insect cells.

3. The vaccine of claim 2, wherein said recombinant baculovirus is identified as AcMNPV.pPPVEx8 and filed with ECACC, accession number V91030213.

4. Empty PPV VP2 capsids consisting of and only autoassembled PPV recombinant VP2 proteins expressed by a recombinant baculovirus in insect cells.

5. Empty VP2 capsids as in claim 4, having a hemagglutination capacity and being immunogenic.

6. Empty VP2 capsids as in claim 4, wherein said recombinant baculovirus is identified as AcMNPV.pPPVEx8 and filed with ECACC, accession number V91030213.

* * * * *